(12) United States Patent
Kawata et al.

(10) Patent No.: US 7,166,096 B2
(45) Date of Patent: Jan. 23, 2007

(54) PULL-ON DISPOSABLE DIAPER WEARING ARTICLE

(75) Inventors: Hikari Kawata, Kagawa-ken (JP); Noriyuki Kurita, Kagawa-ken (JP); Ichiro Wada, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 21 days.

(21) Appl. No.: 10/951,909

(22) Filed: Sep. 29, 2004

(65) Prior Publication Data

US 2005/0055007 A1    Mar. 10, 2005

Related U.S. Application Data

(63) Continuation of application No. PCT/JP03/03265, filed on Mar. 18, 2003.

(30) Foreign Application Priority Data

Mar. 29, 2002    (JP) .............................. 2002-096753

(51) Int. Cl.
*A61F 13/15*    (2006.01)

(52) U.S. Cl. .............................. 604/387; 604/385.201; 604/391

(58) Field of Classification Search ................ 604/387, 604/391, 386, 385.21, 385.201
See application file for complete search history.

(56) References Cited

U.S. PATENT DOCUMENTS

| | | | | |
|---|---|---|---|---|
| 3,776,232 A | * | 12/1973 | Schaar ................... | 604/385.01 |
| 4,475,912 A | * | 10/1984 | Coates ................... | 604/385.15 |
| 4,699,622 A | * | 10/1987 | Toussant et al. ............ | 604/389 |
| 4,883,481 A | * | 11/1989 | Blanchard .............. | 604/385.11 |
| 4,909,803 A | * | 3/1990 | Aziz et al. ............. | 604/385.28 |
| 4,981,480 A | * | 1/1991 | Gaudet et al. .............. | 604/386 |
| 5,342,344 A | * | 8/1994 | Lancaster et al. ........... | 604/387 |
| 5,531,732 A | * | 7/1996 | Wood ......................... | 604/391 |
| 5,591,521 A | * | 1/1997 | Arakawa et al. ............. | 428/352 |
| 5,624,428 A | * | 4/1997 | Sauer ......................... | 604/391 |
| H01674 H | * | 8/1997 | Ames et al. ................ | 604/389 |
| 5,897,545 A | * | 4/1999 | Kline et al. ................. | 604/386 |
| 5,944,707 A | * | 8/1999 | Ronn ......................... | 604/386 |
| 6,102,901 A | * | 8/2000 | Lord et al. .................. | 604/386 |
| 6,287,287 B1 | * | 9/2001 | Elsberg ................. | 604/385.03 |

(Continued)

FOREIGN PATENT DOCUMENTS

JP    06-77718    11/1994

(Continued)

*Primary Examiner*—Tatyana Zalukaeva
*Assistant Examiner*—Paula L. Craig
(74) *Attorney, Agent, or Firm*—Lowe Hauptman & Berner LLP (57) ABSTRACT

A pull-on disposable wearing article has front and rear waist regions and a crotch region extending between the waist regions. Transversely opposite lateral zones of the front and rear waist region are connected to each other in the vicinity of marginal side edges of the lateral zones so as to define a waist-hole and a pair of leg-holes. Hook members used to adjust a waist-circumferential dimension of the article are secured to the front waist region in its lateral zones and loop members on which the hook members are releasably anchored are secured to the front waist region in its middle zone so that the font waist region is normally non-contractible in the waist-circumferential direction.

18 Claims, 10 Drawing Sheets

U.S. PATENT DOCUMENTS

| | | | |
|---|---|---|---|
| 6,375,647 B1* | 4/2002 | Akeno et al. | 604/391 |
| 6,395,115 B1* | 5/2002 | Popp et al. | 156/66 |
| 6,641,568 B1* | 11/2003 | Ashton et al. | 604/385.01 |
| 6,911,023 B1* | 6/2005 | Hamilton et al. | 604/387 |
| 6,972,012 B1* | 12/2005 | Pozniak et al. | 604/386 |
| 2001/0023341 A1* | 9/2001 | Karami | 604/385.03 |
| 2002/0026172 A1* | 2/2002 | Shimada et al. | 604/385.13 |
| 2002/0095131 A1* | 7/2002 | Olson | 604/391 |
| 2002/0099352 A1* | 7/2002 | Heden et al. | 604/387 |
| 2002/0111596 A1* | 8/2002 | Fletcher et al. | 604/385.03 |
| 2002/0123730 A1* | 9/2002 | Popp et al. | 604/385.03 |
| 2002/0123734 A1* | 9/2002 | Carlbark et al. | 604/391 |
| 2003/0100880 A1* | 5/2003 | Magee et al. | 604/389 |

FOREIGN PATENT DOCUMENTS

| | | |
|---|---|---|
| JP | 08-325804 | 12/1996 |
| JP | 09-038134 | 2/1997 |
| JP | 09-206330 | 8/1997 |

* cited by examiner

PULL-ON DISPOSABLE DIAPER WEARING ARTICLE

This application is a continuation of International Application No. PCT/JP03/03265, filed Mar. 18, 2003, which claims priority to Japanese Application No. 2002-96753, filed Mar. 29, 2002.

TECHNICAL FIELD OF THE INVENTION

This invention relates to a pull-on disposable wearing article adapted for absorption and containment of bodily discharges.

BACKGROUND ART OF THE INVENTION

The pull-on disposable wearing article is well known, which is formed of a substantially non-stretchable liquid-pervious topsheet, a substantially non-stretchable liquid-impervious backsheet and the liquid-absorbent panel interposed between these top- and backsheets and having the front and rear waist regions opposed to each other and the crotch region extending between these waist regions, in which transversely opposite lateral zones of the front waist region and transversely opposite lateral zones of the rear waist region are connected together so as to define a waist-hole and a pair of leg-holes.

While the commercially available pull-on disposable wearing articles are different in size depending on whether the article is for children or for adult, these articles are generally mass-produced in predetermined waist-circumferential dimensions for children and for adult and placed on the market, so the articles having a broad range of waist-circumferential dimensions are unavailable. Therefore, the conventional article of this type has necessarily been provided with means functioning to tighten the article around the wearer's torso in order to prevent the article from slipping down along the wearer's body during use of the article.

Examples of the pull-on disposable wearing article provided with such means are disclosed by Japanese Patent Application Nos. 1997-38134A and 1997-206330A. In the articles disclosed therein, a plurality of waist elastic members extending in a waist-circumferential direction are contractibly attached to front and rear waist regions and a plurality of leg elastic members extending in a leg-circumferential direction are contractibly attached to a crotch region in its transversely opposite lateral zones. The waist elastic members are spaced one from another in the longitudinal direction between a waist-hole and leg-holes. These articles make use of a contractile force of the waist elastic members to tighten the wearer's torso and to prevent the article from slipping down along the wearer's body during use of the articles.

In the conventional disposable wearing articles, one of its waist-circumferential dimension and leg-circumferential dimension depends on the other dimension because the wearer's waist-circumferential dimension is correlated with the wearer's leg-circumferential dimension.

In the wearing articles disclosed in the above-cited Application, if a contractile force of the waist elastic members is excessively high, the wearer's torso will be needlessly tightened, the wearer will experience a feeling of incompatibility and even a compression mark will remain on the wearer's body. When it is necessary for a helper to put the article on the wearer's body, the helper must broaden the contracted waist-hole against the contractile force of the waist elastic members to guide the wearer's legs through this broadened waist-hole and then the leg-holes and then pull the article upward to the waist line of the wearer. This may retard the operation of putting the article on the wearer's body and become a burden to the helper.

DISCLOSURE OF THE INVENTION

It is an object of this invention to provide a pull-on disposable wearing article improved so that the article can be easily put on the wearer's body without any anxiety of needlessly compressing the wearer's torso and prevent the article from slipping down along the wearer's body during use of the article.

In accordance with this invention, there is provided a pull-on disposable wearing article comprising: a front waist region; a rear waist region; a crotch region between the front and rear waist regions; a waist-hole; a pair of leg-holes; and one of the front and rear waist regions having a fastening member and a landing member juxtaposed with the fastening member in a waist-circumferential direction of the one of the front and rear waist regions to releasably engage with the fastening members.

This invention includes the following embodiments.

At least one of the front and rear waist regions having the fastening member and the landing member is normally non-contractible in the waist-circumferential direction.

The fastening members are secured to the waist region in the transversely opposite lateral zones and the landing members are secured to the waist region in a middle zone thereof defined between the lateral zones.

The fastening members are spaced from each other in the waist-circumferential direction and secured to the waist region in a middle zone thereof defined between the lateral zones while the landing members are secured to the waist region in the lateral zones thereof and extend in the waist-circumferential direction.

The fastening members obliquely extend from a vicinity of the waist-hole toward the leg-holes so that the fastening members get nearer to a longitudinal center line bisecting the waist-circumferential dimension of the waist region.

The waist region having the fastening members and the landing members has the waist-circumferential dimension larger than that of the waist region having none of these fastening and landing members.

Each of the fastening members is one of a hook member and a loop member constituting so-called a mechanical fastener and each of the landing members is the other of the hook member and the loop member.

Each of the fastening members is a fastener tape made of a plastic material having an outer surface thereof coated with a self-adhesive while each of the landing members is a target tape strip made of the plastic material on which the tape fastener is releasably anchored.

The wearing article is formed of a liquid-pervious topsheet facing a wearer's body, a liquid-impervious backsheet facing away from the wearer's body and a liquid-absorbent panel interposed between the top- and backsheets.

DESCRIPTION OF THE BEST MODE FOR WORKING OF THE INVENTION

Details of a pull-on disposable wearing article according to this invention will be more fully understood from the description given hereunder in reference to the accompanying drawings.

Figure 1:
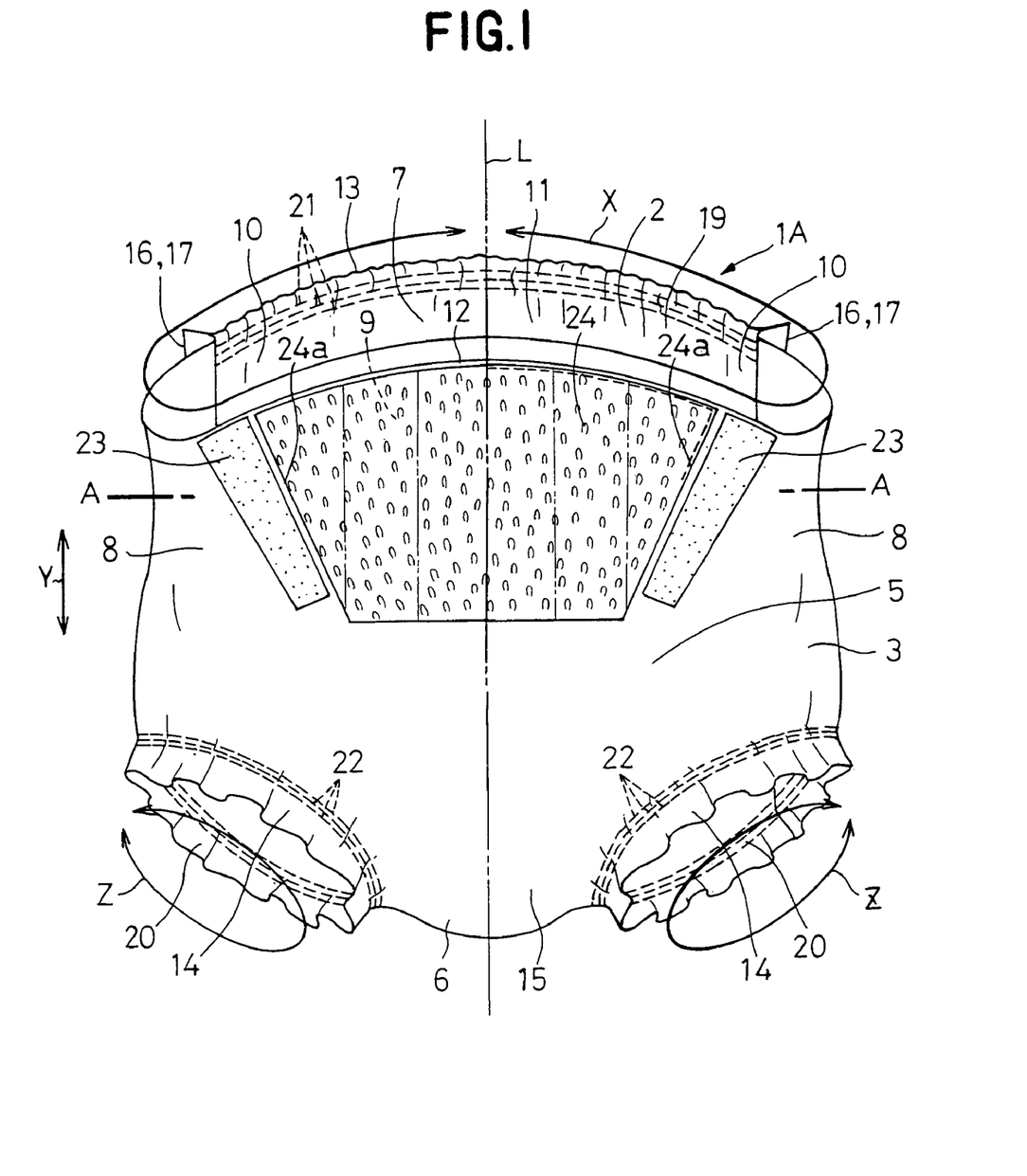
FIG. 1 is a perspective view showing a specific embodiment of a wearing article according to this invention.
Figure 2:
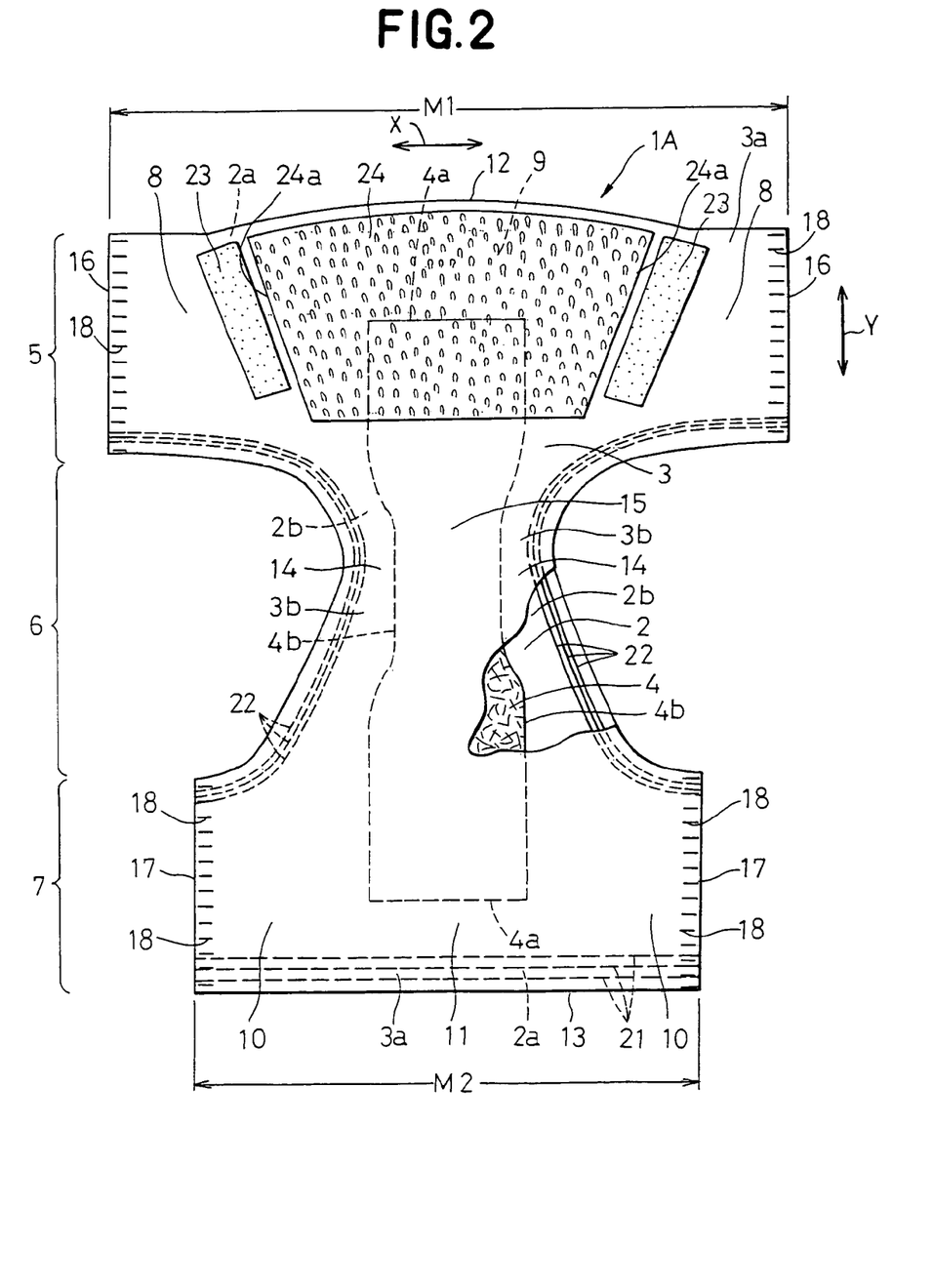
FIG. 2 is a partially cutaway developed plan view showing the article of FIG. 1 with front and rear waist regions disconnected from each other.
Figure 3:
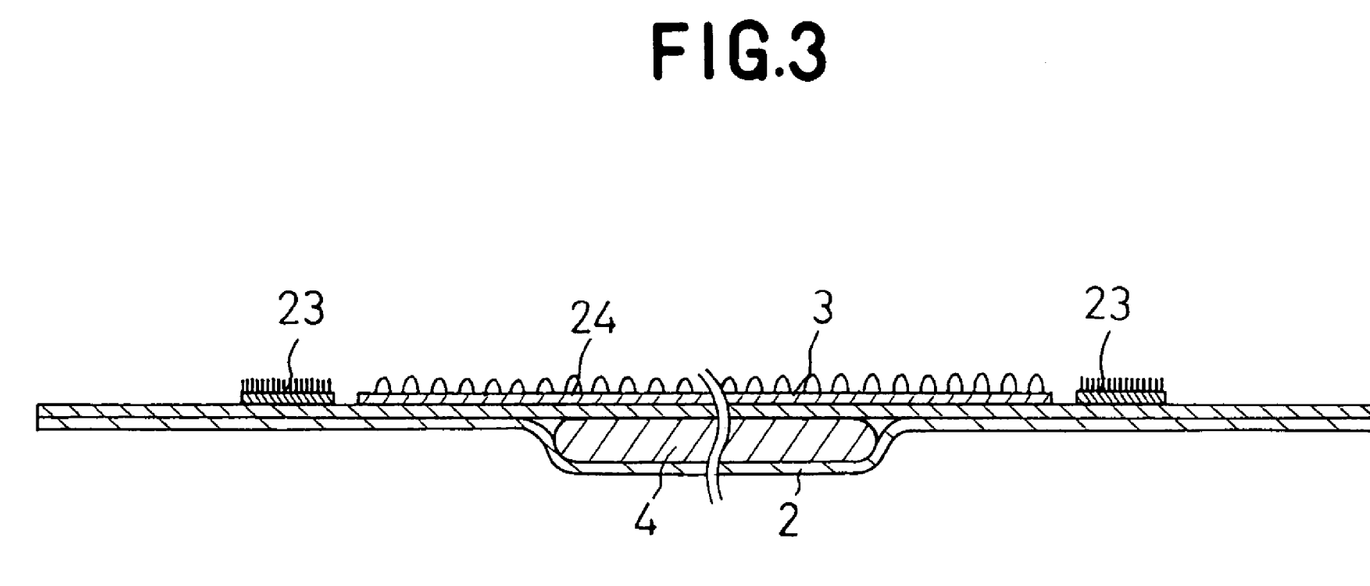
FIG. 3 is a sectional view taken along a line A—A in FIG. 1.

FIG. 1 is a perspective view showing a specific embodiment of the wearing article 1A according to this invention, FIG. 2 is a partially cutaway developed plan view showing the article 1A of FIG. 1 with front and rear waist regions 5, 7 disconnected from each other and FIG. 3 is a sectional view taken along a line A—A in FIG. 1. In FIGS. 1 and 2, a waist circumferential direction is indicated by an arrow X, a longitudinal direction is indicated by an arrow Y and a leg circumferential direction is indicated by an arrow Z (only in FIG. 1). Term "inner surfaces of top- and backsheets 2, 3" used herein refers to the surfaces thereof facing a panel 4 and term "outer surfaces of these sheets 2, 3" refers to the surfaces thereof facing away from the panel 4.

The article 1A comprises a substantially non-stretchable liquid-pervious topsheet 2, a substantially non-stretchable liquid-impervious backsheet 3 and a liquid-absorbent panel 4 interposed between the top- and backsheets 2, 3 and secured to the inner surface of at least one of these sheets 2, 3. The article 1A has front and rear waist regions 5, 7 opposed to each other and a crotch region 6 extending between these waist regions 5, 7.

The front and rear waist regions 5, 7 respectively have waist-circumferential transversely opposite lateral zones 8, 10 and waist-circumferential middle zones 9, 11 extending between the respective lateral zones 8, 10. The lateral zones 8, 10 extend outward from lateral boundaries of the respective middle zones 9, 11 in waist-circumferential direction. A longitudinal end 12 of the front waist region 5 curves so as to describe a circular arc which is convex upward in the longitudinal direction as this end 12 extends from the opposite lateral zones 8 toward the middle zone 9. The crotch region 6 has leg-circumferential transversely opposite lateral zones 14 each extending in a leg-circumferential direction and a leg-circumferential middle zone 15 extending between these opposite lateral zones 14. The panel 4 extends over the crotch region 6 into the front and rear waist regions 5, 7 so as to be continuously laid on the respective middle zone 9, 11, 15.

As will be apparent from FIG. 2, the opposite lateral zones 14 of the crotch region 6 curve inward to describe circular arcs as viewed in the waist-circumferential direction of the article 1A so that the article 1A has a substantially hourglass-like planar shape. In the article 1A, a waist-circumferential dimension M1 of the front waist region 5 is larger than a waist-circumferential dimension M2 of the rear waist region 7.

In the article 1A, the lateral zones 8 of the front waist region 5 and the lateral zones 10 of the rear waist region 7 are overlaid and joined together in the vicinity of the outermost edges 16, 17 of these lateral zones 8, 10, respectively, by means of a plurality of heat-sealing lines 18 intermittently arranged in the vicinity of these outermost edges 16, 17. The article 1A is formed with a waist-hole 19 and a pair of leg-holes 20. While the waist-circumferential dimension necessarily depends on the leg-circumferential dimension in the well-known disposable wearing article, this invention advantageously ensures the waist-circumferential dimension to be appropriately larger than the waist-circumferential dimension of the wearer even when the leg-circumferential dimension of the article 1A conforms with that of this wearer.

The rear waist region 7 is provided in the vicinity of its longitudinal end 13 with a plurality of waist elastic members 21 extending in the waist-circumferential direction and contractibly secured thereto. Contractile force of these waist elastic members 21 normally biases the rear waist region 7 to contract inward as viewed in the waist-circumferential direction. Each of the lateral zones 14 in the crotch region 6 is provided with a plurality of leg elastic members 22 extending in the leg-circumferential direction and contractibly secured thereto. Contractile force of these leg elastic members 22 normally biases the lateral zone 14 to contract inward in the leg-circumferential direction.

The front waist region 5 has hook members 23 (fastening members) and a loop member 24 (landing member) juxtaposed with the hook members 23 in the waist-circumferential direction, which are secured thereto so as to be releasably engaged with each other for the purpose of adjusting a waist-circumferential dimension of the article 1A. The front waist region 5 has none of the waist elastic members secured thereto and therefore the front waist region 5 is not biased to contract inward in the waist-circumferential direction.

The hook members 23 are belt-shaped and extend in the longitudinal direction between the waist-hole 19 and the respective leg-holes 20. The hook members 23 are secured to the front waist region 5 in the opposite lateral zones 8. These hook members 23 obliquely extend from the vicinity of the waist-hole 19 toward the respective leg-holes 20 so that these hook members 23 progressively get nearer to a longitudinal center line L bisecting a waist-circumferential dimension M1 of the front waist region 5.

The loop member 24 is of a substantially rectangular shape having its longer sides oriented in the waist-circumferential direction and extends in this direction between the pair of hook members 23. This loop member 24 is secured to the front waist region 5 over the substantially entire middle zone 9 thereof. Transversely opposite side edges 24a of the loop member 24 opposed to the respective hook members 23 obliquely extend from the vicinity of the waist-hole 19 toward the respective leg-holes 20 so that these side edges 24a get nearer to the longitudinal center line L. The hook members 23 and the loop member 24 are secured to the outer surface of the backsheet 3 by means of hot melt adhesives (not shown).

In this article 1A, it is also possible to secure a pair of loop members 24 to the front waist region 5 in its lateral zones 8 and to secure a single hook member 23 to the front waist region 5 in its middle zone 9. Moreover, it is also possible that one of the hook member(s) 23 and the loop member(s) 24 are secured to the rear waist region 7 in its lateral zones 10 and the other of these members 23, 24 is secured to the rear waist region 7 in its middle zone 11, instead of securing these hook and loop members 23, 24 to the front waist region 5.

Along the longitudinal ends 12, 13 of the front and rear waist regions 5, 7, respectively, the top- and backsheets 2, 3 extend in the longitudinal direction beyond longitudinally opposite ends 4a of the panel 4 so as to define respective marginal ends 2a, 3a having inner surfaces thereof bonded together. Waist elastic members 21 are interposed between the marginal ends 2a, 3a of the top-and backsheets 2, 3 and secured to the inner surfaces of these marginal ends 2a, 3a of these sheets 2, 3.

In the lateral zones 8, 10 of the front and rear waist regions 5, 7, respectively, and in the lateral zones 14 of the crotch region 6, the top- and backsheets 2, 3 extend outward in the waist-circumferential direction beyond transversely opposite side edges 4b of the panel 4 so as to define marginal side edges 2b, 3b, respectively, having inner surfaces firmly bonded together. Leg elastic members 22 are interposed between these marginal side edges 2b, 3b of the top- and backsheets 2, 3 and secured to inner surfaces of these marginal side edges 2b, 3b of the respective sheets 2, 3.

Figure 4:
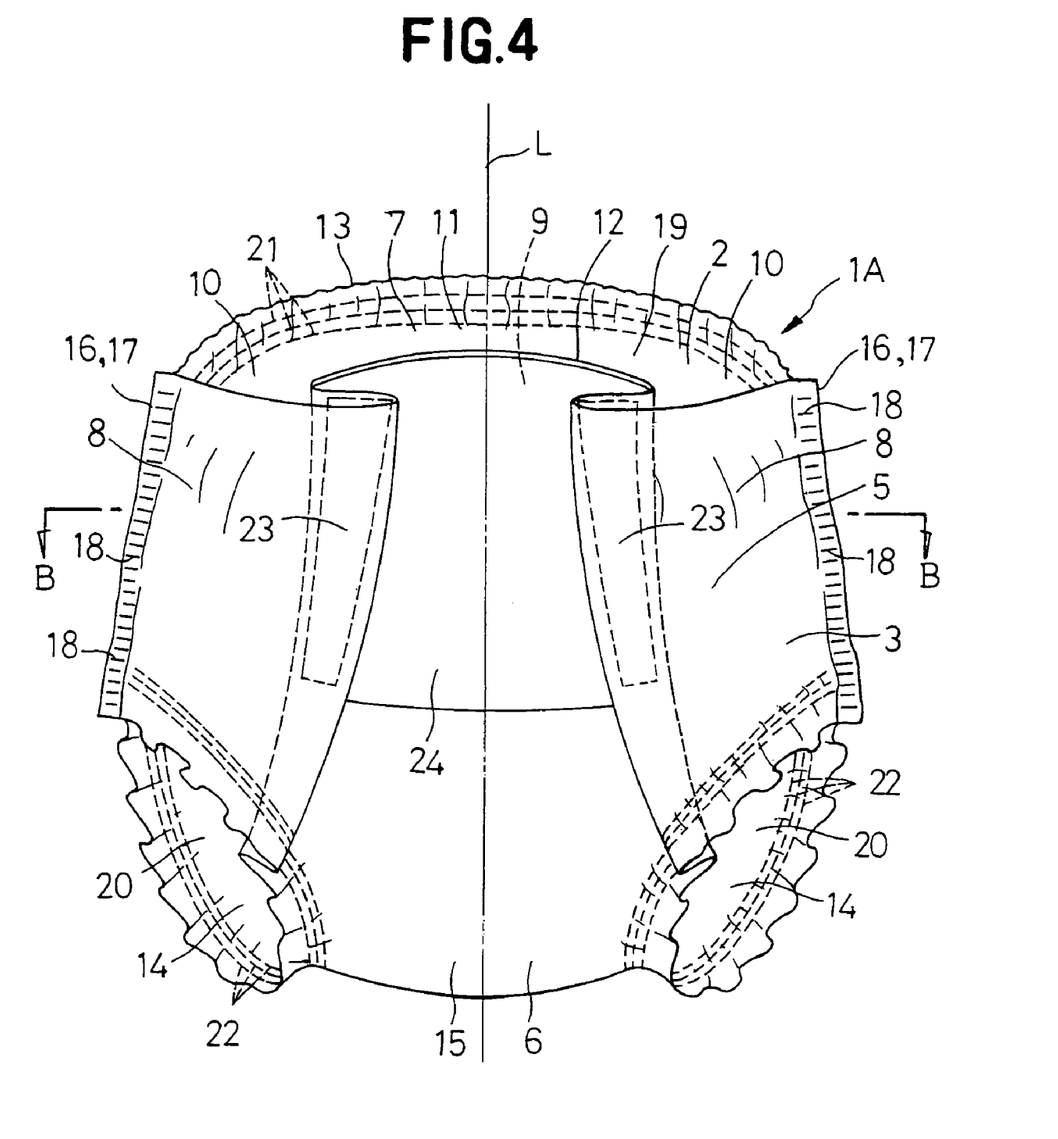
FIG. 4 is a perspective view showing the article of FIG. 1 as hook members have been anchored on loop members.
Figure 5:
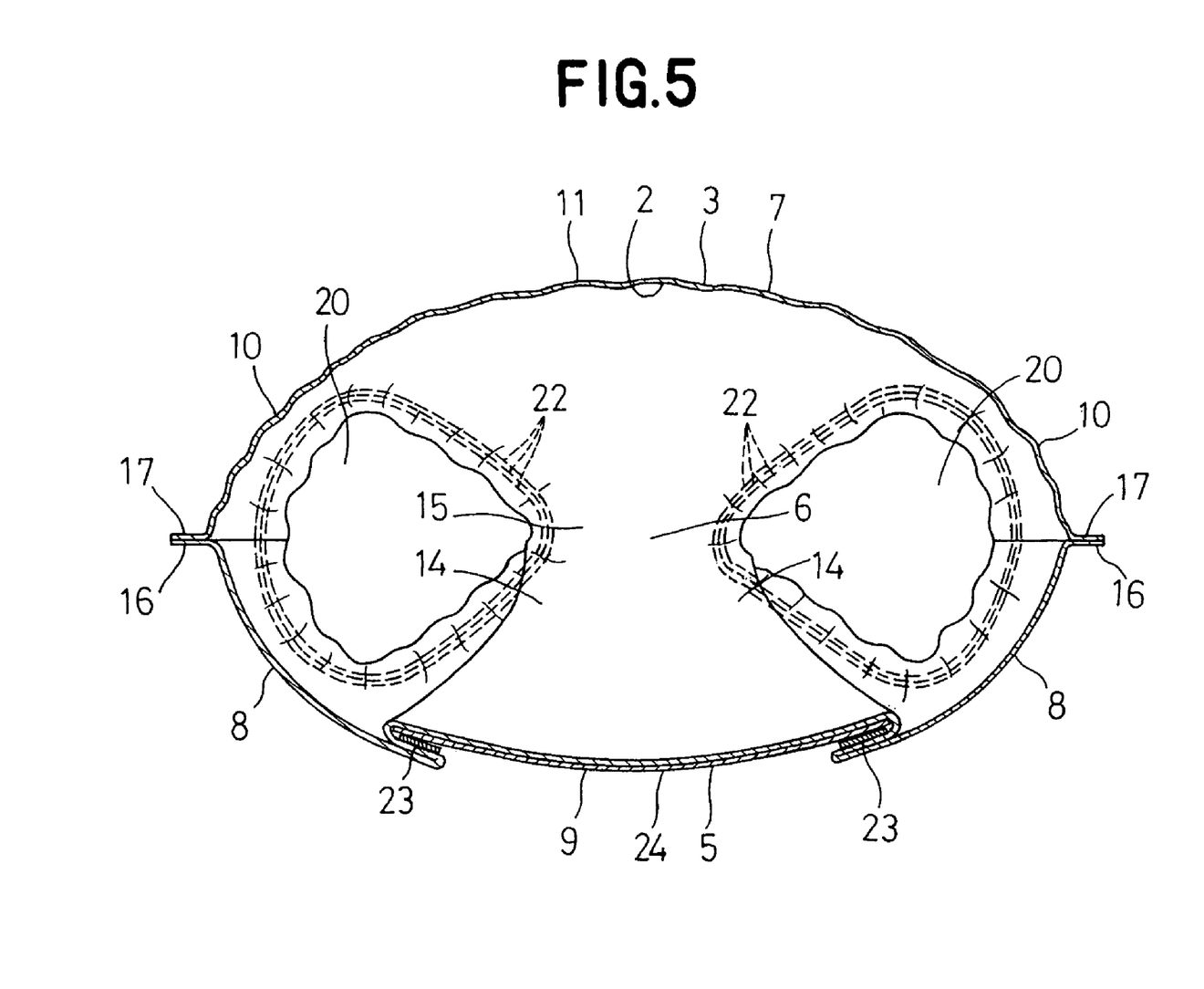
FIG. 5 is a sectional view taken along a line B—B in FIG. 4.

FIG. 4 is a perspective view showing the article 1A of FIG. 1 as the hook members 23 have been anchored on the loop member 24 and FIG. 5 is a sectional view taken along a line B—B in FIG. 4. When it is desired for a helper to put the article 1A on a wearer's body, the helper guides the wearer's legs to pass through the waist-hole 19 and then through the leg-holes 20. Thereupon the helper pulls the article 1A upward along the wearer's body. Then the helper puts the lateral zones 8 of the front waist region 5 onto the outer side of the middle zone 9 of the same waist region 5 and thereby adjusts the waist-circumferential dimension of the article 1A so that the wearer's torso may be moderately compressed. Finally, the hook members 23 are anchored on the loop member 24. In the article 1A put on the wearer's body, the lateral zones 8 and the middle zone 9 are partially fastened together by means of the hook members 23 and the loop member 24 so as to present substantially Z-shaped cross-sections.

Positions at which the respective hook members 23 should be anchored on the loop member 24 may be selected to adjust the waist-circumferential dimension of the article 1A depending on a waist-circumferential dimension of the particular wearer. In other words, the article 1A can be prevented from unintentionally slipping down without relying upon a contractile force of the waist elastic members. In contrast with the conventional article in which the front and rear waist regions are provided with a plurality of waist elastic members extending in the waist-circumferential direction and secured thereto under tension, the article 1A is free from not only an anxiety that the torso of the wearer might be needlessly compressed but also an anxiety that the wearer might experience a feeling of incompatibility. Furthermore, it is not likely that any compression mark might remain on the body of the wearer.

When the article 1A is put on the wearer's body, it is unnecessary to broaden the waist-hole against a contractile force of the waist elastic members as the conventional article has been the case, since the front waist region 5 does not contract inward in the waist-circumferential direction. Consequently, it is not likely that the operation of putting the article 1A on the wearer's body might be retarded and become a burden to the helper.

In the article 1A, the waist-circumferential dimension M1 of the front waist region 5 is larger than that of the rear waist region 7 and the waist-circumferential dimension M1 of the front waist region 5 may be used to adjust the waist-circumferential dimension of the article 1A within a wide range. With this article 1A, the waist-circumferential dimension of the article 1A is normally larger than the waist-circumferential dimension of the wearer. This unique feature facilitates the helper to guide the wearer's legs through the waist-hole 19 as well as through the leg-holes and then to pull the article 1A upward along the wearer's body.

In the article 1A, the hook members 23 secured to the front waist region 5 in its lateral zones 8 obliquely extend from the vicinity of the waist-hole 19 toward the leg-holes 20 so that these hook members 23 progressively get nearer to the longitudinal center line L. If the hook members 23 are anchored on the loop member 24 so that the hook members 23 extend substantially in parallel to the longitudinal center line L, the waist-circumferential dimension M1 of the front waist region 5 as measured in the vicinity of the crotch region 6 will be larger than the dimension M1 of the front waist region 5 in the vicinity of its longitudinal end 12. This means that, even if the wearer's torso is somewhat tightly compressed by the portion of the front waist region 5 lying in the vicinity of the end 12, there is no possibility that the wearer's lower abdomen might be tightly compressed by the portion of the front waist region 5 lying in the vicinity of the crotch region 6. As a result, the lower abdomen of the wearer will be free from any oppressive feeling.

Figure 6:
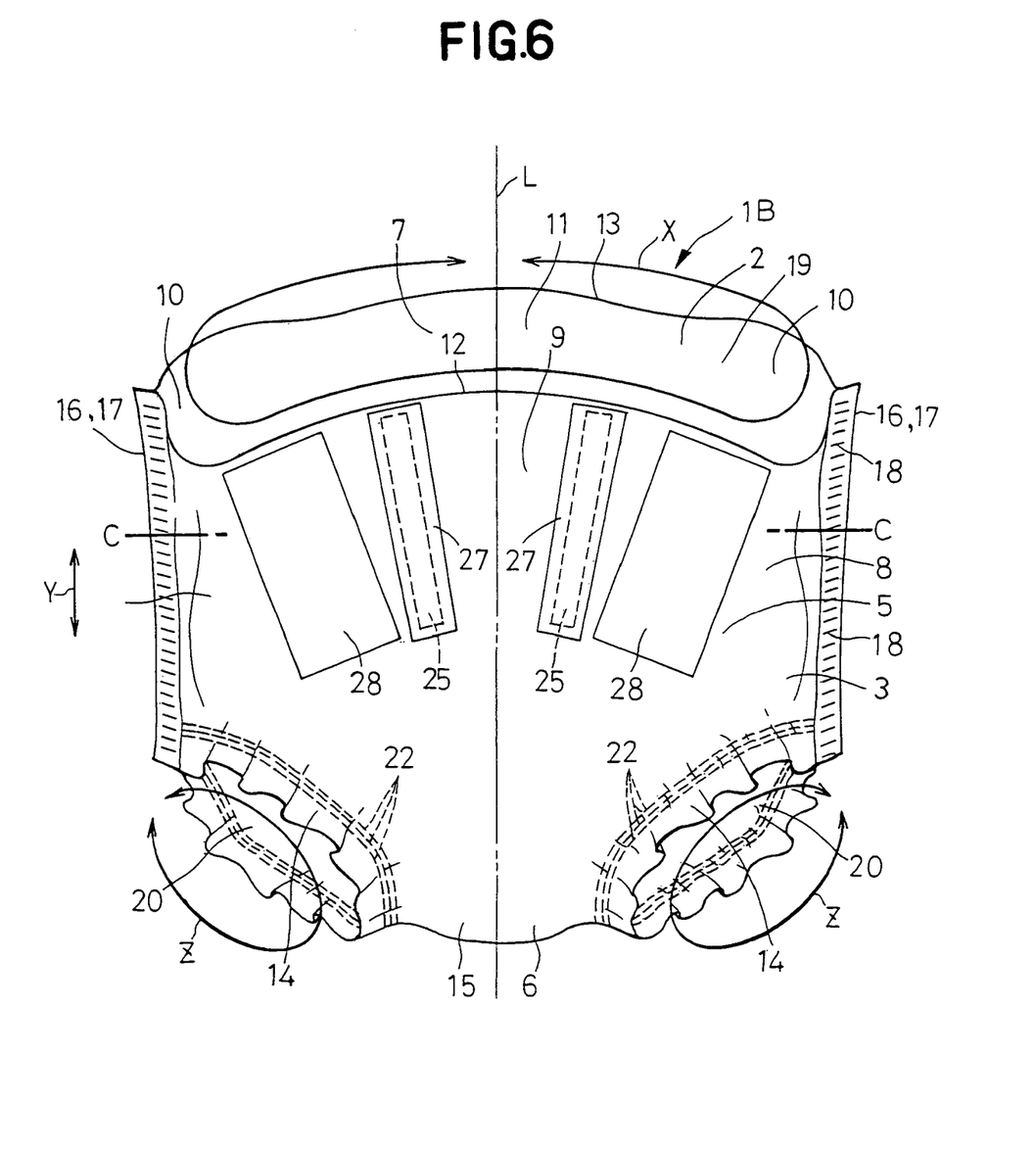
FIG. 6 is a perspective view showing another embodiment of the article according to this invention.
Figure 7:
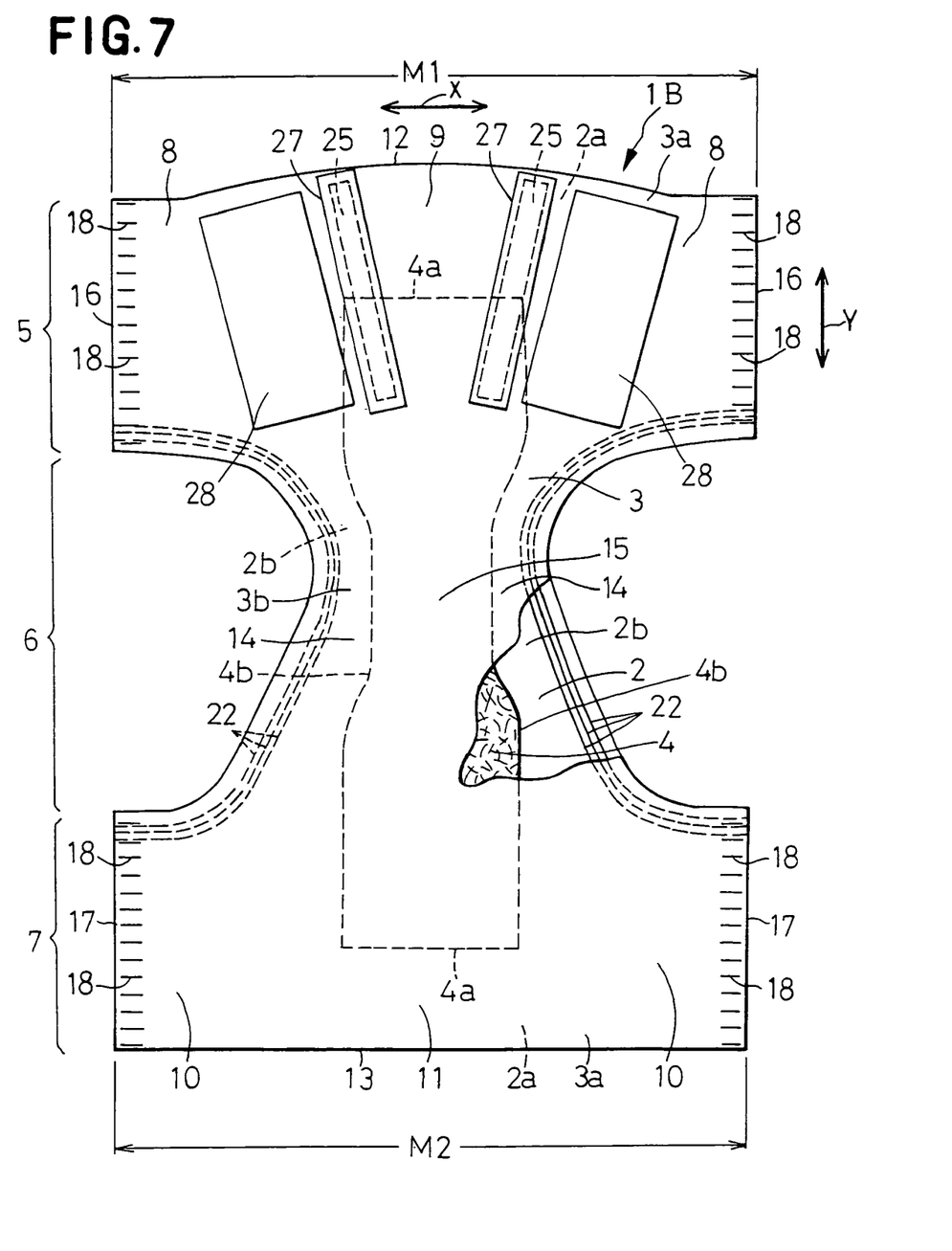
FIG. 7 is a partially cutaway developed plan view showing the article of FIG. 6 with front and rear waist regions disconnected from each other.
Figure 8:
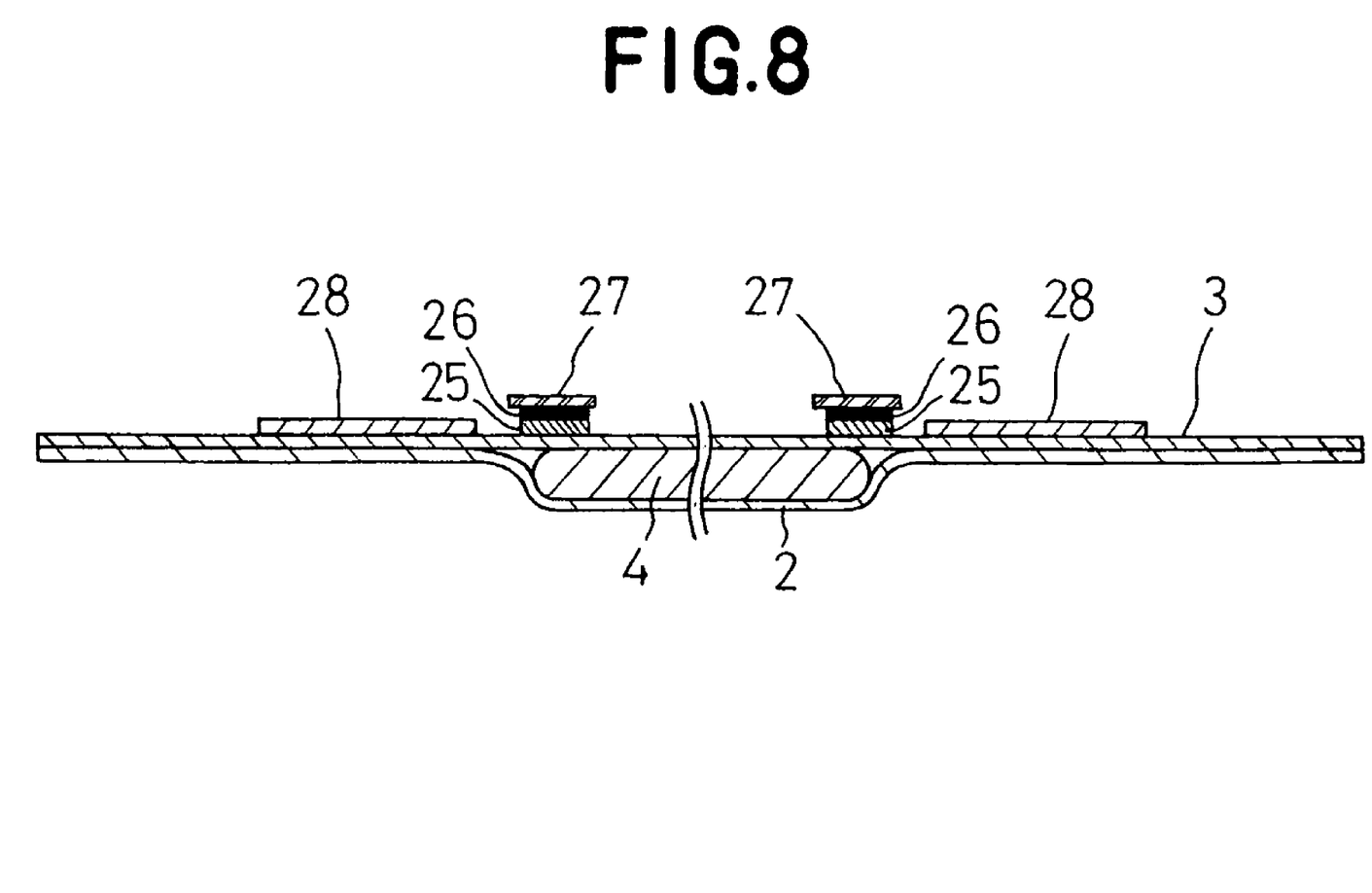
FIG. 8 is a sectional view taken along a line C—C in FIG. 6.

FIG. 6 is a perspective view showing another embodiment 1B of the article according to this invention, FIG. 7 is a partially cutaway developed plan view showing the article 1B of FIG. 6 with the front and rear waist regions 5, 7 disconnected from each other and FIG. 8 is a sectional view taken along a line C—C in FIG. 6. In FIGS. 6 and 7, the waist-circumferential direction is indicated by an arrow X, the longitudinal direction is indicated by an arrow Y and the leg-circumferential direction is indicated by an arrow Z (only in FIG. 6).

The article 1B comprises a substantially non-stretchable liquid-pervious topsheet 2, a substantially non-stretchable liquid-impervious backsheet 3 and a liquid-absorbent panel 4 interposed between the top- and backsheets 2, 3. Both the topsheet 2 and the backsheet 3 are elastically stretchable in the longitudinal direction as well as in the waist-circumferential direction. The article 1B has front and rear waist regions 5, 7 opposed to each other and a crotch region 6 extending between these waist regions 5, 7. The front and rear waist regions 5, 7 respectively have transversely opposite lateral zones 8, 10 which are joined together in the vicinity of the marginal side edges 16, 17 thereof by means of a plurality of heat-sealing lines arranged intermittently along these marginal side edges 16, 17. The article 1B is formed with the waist-hole 19 and the pair of leg-holes 20. In the article 1B, the waist-circumferential dimension M1 of the front waist region 5 is substantially same as the waist-circumferential dimension M2 of the rear waist region 7.

The lateral zones 14 are respectively provided with a plurality of leg elastic members 22 extending in the leg-circumferential direction and contractibly secured thereto. The lateral zones 14 are normally contracted inward in the leg-circumferential direction under a contractile force of these leg elastic members 22. The front waist region 5 is provided with fastener tapes 25 (fastening members) used to adjust the waist-circumferential dimension of the article 1B and target tape strips 28 (landing members) with which the fastener tapes 25 are releasably engaged. Both the front waist region 5 and the rear waist region 7 include none of the waist elastic members and normally in non-contracted state.

The fastener tapes 25 are made of a flexible plastic film and coated on the outer surfaces thereof with a self-adhesive 26. The fastener tapes 25 are in the form of belt-like shape and extend in the longitudinal direction between the waist-hole 19 and the leg-holes 20. Specifically, the fastener tapes 25 are spaced from and opposed to each other in the waist-circumferential direction and secured to the front waist region 5 in the middle zone 9 defined between the lateral zones 8. The fastener tapes 25 obliquely extend from the vicinity of the waist-hole 19 toward the leg-holes 20 so that fastener tapes 25 progressively get nearer to the longitudinal center line L. The self-adhesive 26 is protectively covered with release paper 27.

The target tape strips 28 are made of the flexible plastic film. The target tape strips 28 are in the form of rectangular shape and secured to the front waist region 5 in the lateral zones 8 so as to extend in the waist-circumferential direction. Specifically, the target tape strips 28 obliquely extend from the vicinity of the waist-hole 19 toward the leg-holes 20 so that the target tape strips 28 progressively get nearer to the longitudinal center line L. The fastener tapes 25 and the target tape strips 28 are secured to the outer surface of the backsheet 3 by means of adhesives (not shown).

It is possible to construct the article 1B so that, instead of securing the fastener tapes 25 and the target tape strips 28 to the front waist region 5, the fastener tapes 25 are secured to the rear waist region 7 in its middle zone 11 defined between the lateral zones 10 and the target tape strips 28 are secured to the rear waist region 7 in its lateral zones 10.

Figure 9:
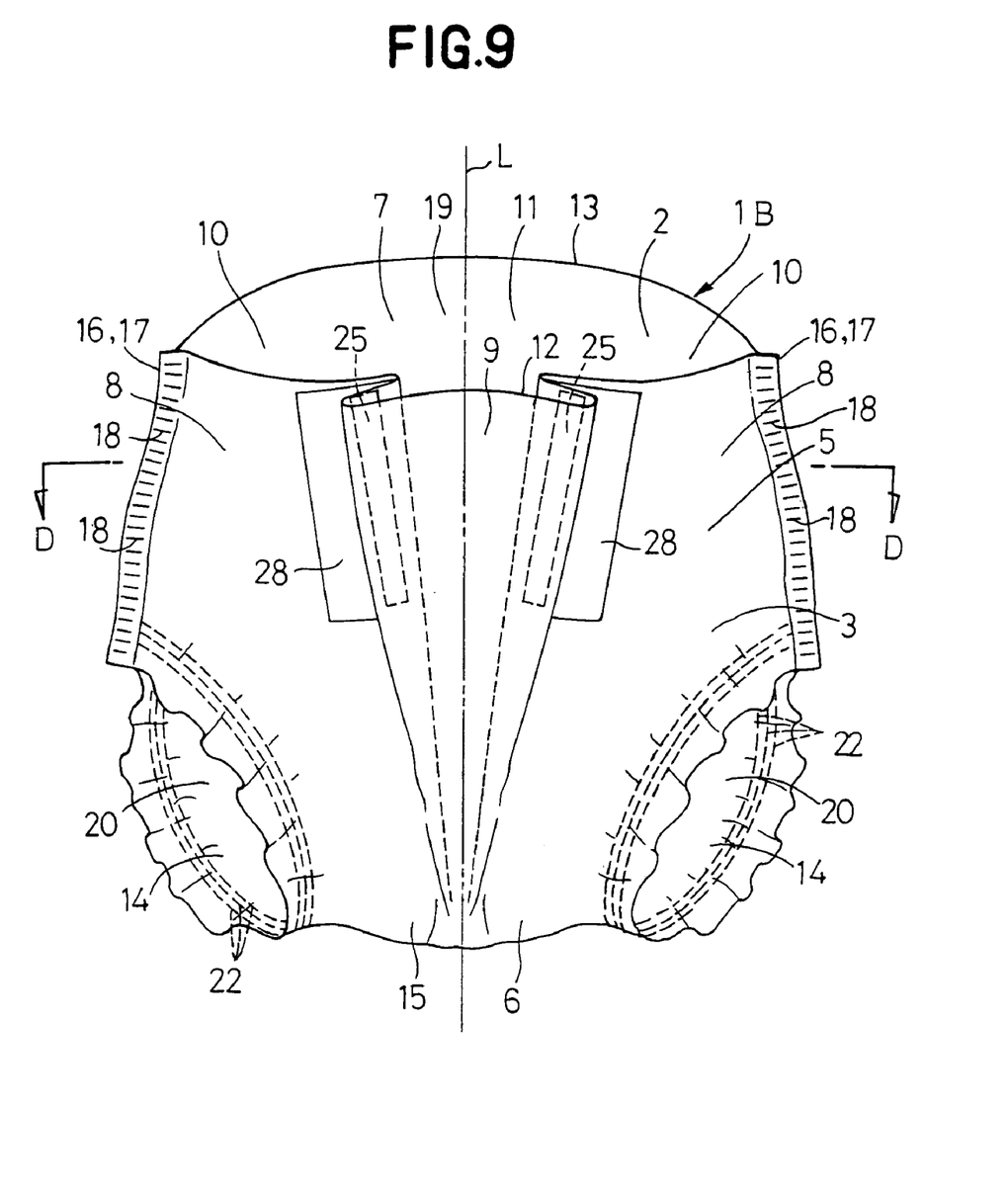
FIG. 9 is a perspective view showing the article of FIG. 6 as put on the wearer's body with the tape fasteners anchored on the target tape strip.
Figure 10:
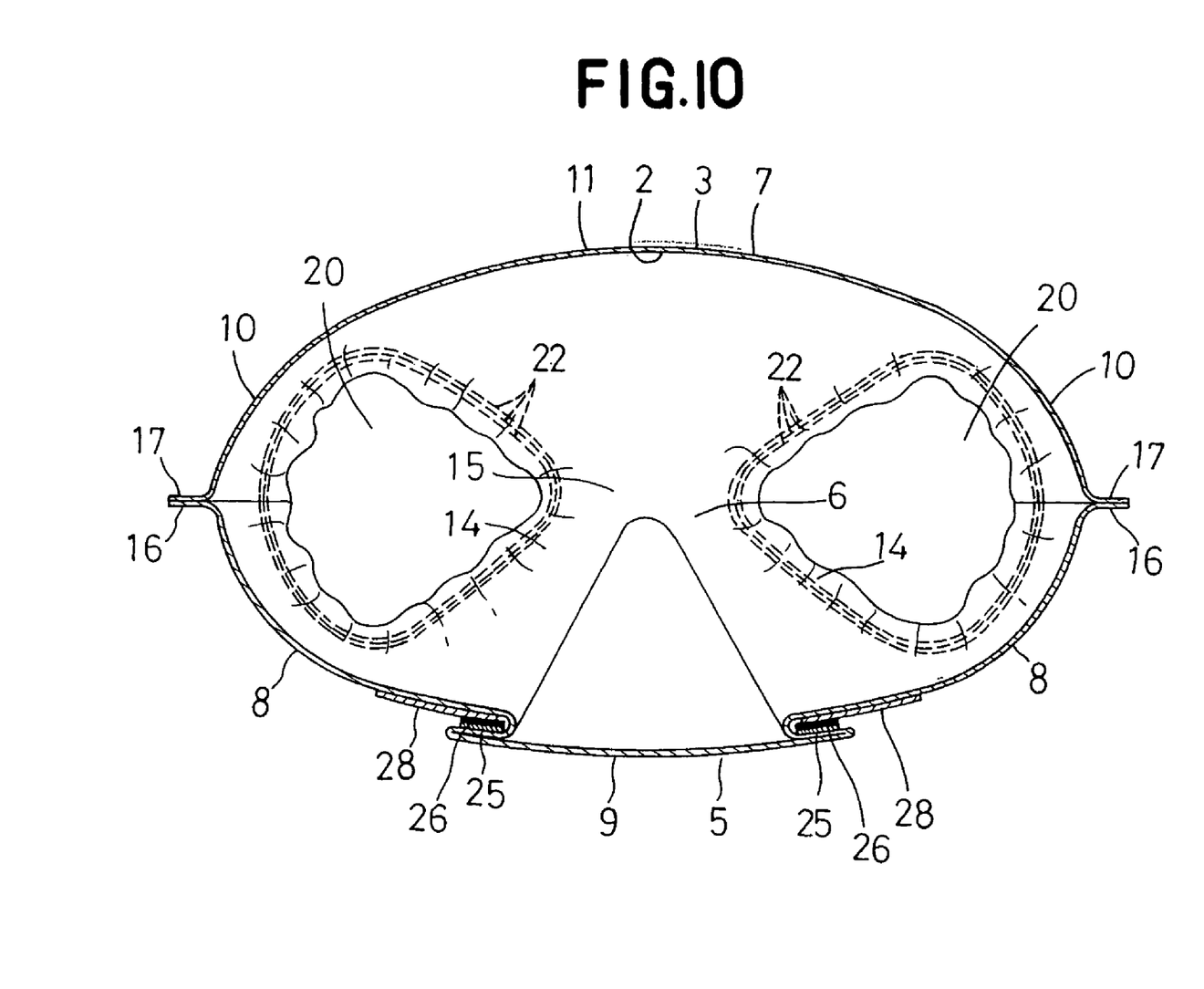
FIG. 10 is a sectional view taken along a line D—D in FIG. 9.

FIG. 9 is a perspective view showing the article 1B of FIG. 6 as put on the wearer's body with the fastener tapes 25 anchored on the target tape strip 28 and FIG. 10 is a sectional view taken along a line D—D in FIG. 9. When it is desired for the helper to put the article 1B on the wearer's body, the helper guides the wearer's legs to pass through the waist-hole 19 and then through the leg-holes 20. Thereupon the helper pulls the article 1B upward along the wearer's body. Then the helper peels off the release paper 27 from the fastener tapes 25 to expose the self-adhesive 26 and puts the middle zone 9 of the front waist region 5 onto the outer sides of the respective lateral zones 8. Thereby the helper adjusts the waist-circumferential dimension of the article 1B and then anchors the fastener tapes 25 on the target tape strips 28 by means of the self-adhesive 26. With the article 1B put on the wearer's body, the lateral zones 8 and the middle zone 9 are partially overlaid by means of the fastener tapes 25 and the target tape strips 28 so as to present substantially Z-shaped cross-sections as best seen in FIG. 10.

Positions at which the respective fastener tapes 25 should be anchored on the target tape strips 28 may be selected to adjust the waist-circumferential dimension of the article 1B depending on a waist-circumferential dimension of the particular wearer. In other words, the article 1B can be prevented from unintentionally slipping down without relying upon a contractile force of the waist elastic members. In contrast with the conventional article in which the front and rear waist regions are provided with a plurality of waist elastic members extending in the waist-circumferential direction and secured thereto under tension, the article 1B is free from not only an anxiety that the torso of the wearer might be needlessly compressed but also an anxiety that the wearer might experience a feeling of incompatibility. Furthermore, it is not likely that any compression mark might remain on the body of the wearer.

When the article 1B is put on the wearer's body, it is unnecessary to broaden the waist-hole against a contractile force of the waist elastic members as the conventional article has been the case, since both the front waist region 5 and the rear waist region 7 do not contract inward in the waist-circumferential direction. Consequently, it is not likely that the operation of putting the article 1B on the wearer's body might be retarded and become a burden to the helper.

In the article 1B, the fastener tapes 25 secured to the front waist region 5 in its middle zone 9 obliquely extend from the vicinity of the waist-hole 19 toward the leg-holes 20 so that these fastener tapes 25 get nearer to the longitudinal center line L. If the fastener tapes 25 are anchored on the target tape strips 28 so that the fastener tapes 25 extend substantially in parallel to the longitudinal center line L, the waist-circumferential dimension M1 of the front waist region 5 as measured in the vicinity of the crotch region 6 will be larger than the dimension M1 of the front waist region 5 in the vicinity of its longitudinal end 12. There is no possibility that the wearer's lower abdomen might be tightly compressed by the portion of the front waist region 5 lying in the vicinity of the crotch region 6. As a result, the lower abdomen of the wearer will be free from any oppressive feeling.

The topsheet 2 of the article 1A shown in FIG. 1 may be formed of a material selected from the group including a hydrophilic fibrous nonwoven fabric, a hydrophobic fibrous nonwoven fabric having a plurality of fine apertures and a liquid-pervious plastic film having a plurality of fine pores. The backsheet 3 of the article 1A shown in FIG. 1 may be formed of a material selected from the group including a hydrophobic fibrous nonwoven fabric, a breathable liquid-impervious plastic film, two or more layers of hydrophobic fibrous nonwoven fabrics laminated one with another and a composite sheet consisting of a hydrophobic fibrous nonwoven fabric and a breathable liquid-impervious plastic film. It is also possible to form the backsheet 3 using a composite nonwoven fabric comprising a melt blown fibrous nonwoven fabric having a high water-resistance and spun bond fibrous nonwoven fabrics having a high strength and a flexibility sandwiching the melt blown fibrous nonwoven fabric therebetween.

Nonwoven fabric may be selected from the group including products obtained by spun lacing, needle punching, melt blowing, thermal bonding, spun bonding, chemical bonding and air-through processes. Component fibers of the nonwoven fabric may be selected from the group including polyolefine-, polyester- and polyamide-based fibers and core-sheath-type and side-by-side-type conjugated fibers of polyethylene/polypropylene and polyethylene/polyester.

The topsheet 2 of the article 1B shown in FIG. 6 may be formed of a stretchable hydrophilic fibrous nonwoven fabric. The backsheet 3 of the article 1B shown in FIG. 6 may be formed of a material selected from the group including a stretchable hydrophobic fibrous nonwoven fabric, a stretchable liquid-impervious plastic film, a composite nonwoven fabric comprising two layers of stretchable hydrophobic fibrous nonwoven fabrics overlaid each other, a composite film comprising two layers of stretchable liquid-impervious plastic film overlaid each other, and a composite sheet comprising stretchable hydrophobic fibrous nonwoven fabrics and stretchable liquid-impervious plastic films overlaid each other. The stretchable fibrous nonwoven fabric may be product obtained by melt blowing or spun bonding process. Component fibers of the stretchable nonwoven fabric may be stretchable fibers obtained by melt spinning thermoplastic elastomer resin.

It is also possible to form the backsheet 3 of the article 1B shown in FIG. 6 using a composite nonwoven fabric obtained by laminating hydrophobic fibrous nonwoven fabrics made of crimped fibers which are obtained, in turn, by melt spinning a thermoplastic synthetic resin of polypropylene, polyethylene or polyester to at least one surface of a stretchable hydrophobic fibrous nonwoven fabric made of thermoplastic elastomer resin fibers.

The liquid-absorbent panel 4 is a mixture of fluff pulp and super-absorbent polymer particles or a mixture of fluff pulp, super-absorbent polymer particles and thermoplastic synthetic resin fibers, in both cases, compressed to a desired thickness. Preferably, the panel 4 is entirely enwrapped with a liquid-pervious sheet such as a tissue paper or a hydrophilic fibrous nonwoven fabric in order to prevent the panel 4 from getting out of its desired shape and/or to prevent the polymer particles from falling off from the panel 4. The polymer particles may be selected from the group consisting of a starch-based polymer, a cellulose-based polymer or a synthetic polymer.

To join the top- and backsheets 2, 3, to secure the panel 4 to the top- and backsheets 2, 3, and to secure the elastic members 21, 22 to the top- and backsheets 2, 3, hot melt adhesives or welding means such as heat-sealing and sonic-sealing may be used.

The disposable wearing article according to this invention includes, in any one of the front and rear waist regions, the fastening member and the landing member for this fastening member adapted to be releasably engaged with each other and used to adjust the waist-circumferential dimension of the article. The relative position of the fastening member and the landing member at which they should be engaged with each other may be selected to adjust the waist-circumferential dimension of the article depending on the waist-circumferential dimension of the particular wearer. In other words, the article can be prevented from unintentionally slipping down without the anxiety that the torso of the wearer might be needlessly compressed. In this way, there is no anxiety that the wearer might experience a feeling of incompatibility and any compression mark might remain on the body of the wearer.

In this article, at least one of the front and rear waist regions which is provided with the fastening member and the landing member is normally non-contractible in the waist-circumferential direction. Therefore, when the article is put on the wearer's body, it is unnecessary to broaden the waist-hole against a contractile force of the waist elastic members as the conventional article has been the case. Consequently, it is not likely that the operation of putting the article on the wearer's body might be retarded and become a burden to the helper.

In the embodiment of the article in which the waist region having the fastening member and the landing member secured thereto has its waist-circumferential dimension larger than that of the other waist region, the full waist-circumferential dimension of the former may be used to adjust the waist-circumferential dimension of the article over a wide range. This article normally has the waist-circumferential dimension larger than the waist-circumferential dimension of the wearer's waist-circumferential dimension. Such feature facilitates the helper to guide the wearer's legs through the waist-hole, on one hand, and facilitates the helper to pull the article upward around the wearer's body.

In the article in which the fastening member obliquely extends from the vicinity of the waist-hole toward the leg-holes so that the fastening member progressively get nearer to the longitudinal center line. If the fastening member is anchored on the landing member so that the fastening member extends substantially in parallel to the longitudinal center line, the waist-circumferential dimension of the waist region as measured in the vicinity of the crotch region will be larger than the dimension of the waist region in the vicinity of its longitudinal end. In this way, there is no possibility that the wearer's lower abdomen might be tightly compressed by the portion of the waist region lying in the vicinity of the crotch region and the wearer might experience an oppressive feeling on the lower abdomen.

What is claimed is:

1. A pull-on disposable wearing article, comprising:
   a front waist region;
   a rear waist region;
   a crotch region extending in a longitudinal direction between said front and rear waist regions;
   one of said front and rear waist regions having opposite inner and outer surfaces, the inner surface facing the other one of said front and rear waist regions, the outer surface facing away from the other one of said front and rear waist regions;
   said one of said front and rear waist regions comprising on the outer surface thereof:
   at least a first fastening member, and
   at least a second fastening member which is juxtaposed with said first fastening member in a transverse direction of the one of said front and rear waist regions;
   wherein each of said first and second fastening members comprises a base sheet and a first or second fastening element, respectively;
   the base sheet having opposite inner and outer surfaces, the inner surface of said base sheet facing and being bonded to the outer surface of the one of said front and rear waist regions, the outer surface of said base sheet facing away from the one of said front and rear waist regions;
   the first or second fastening element being disposed on the outer surface of the respective base sheet in the portion where the inner surface of said base sheet is bonded to the outer surface of the one of said front and rear waist regions; and
   the first fastening element of the first fastening member being releasably engageable with the second fastening element of the second fastening member.

2. The wearing article according to claim 1, wherein the one of said front and rear waist regions is free of elastic material and is non-contractible in said transverse direction.

3. The wearing article according to claim 1, comprising two said first fastening members which are secured to transversely opposite lateral zones of the one of said front and rear waist regions;
   wherein said second fastening member is secured to a middle zone of the one of said front and rear waist regions, said middle zone being located between said lateral zones.

4. The wearing article according to claim 3, comprising two said second fastening members which are spaced from each other in said transverse direction and secured to said middle zone.

5. The article according to claim 3, wherein the second fastening element extends continuously in said middle zone and across a longitudinal center line bisecting a width, measured in said transverse direction, of the one of said front and rear waist regions.

6. The article according to claim 5, wherein said second fastening member is a loop member and said first fastening members are hook members.

7. The article according to claim 5, wherein
a length, measured in the longitudinal direction, of said second fastening member is greater than that of each of said first fastening members; and
a width, measured in the transverse direction, of said second fastening member is greater than that of each of said first fastening members.

8. The wearing article according to claim 1, wherein the one of said front and rear waist regions that has said first and second fastening members has a dimension in said transverse direction larger than that of the other one of said front and rear waist regions.

9. The wearing article according to claim 1, wherein
said first fastening member is a hook member and said first fastening element comprises hooks; and
said second fastening member is a loop member and second first fastening element comprises loops releasably engageable with said hooks.

10. The wearing article according to claim 1, wherein
said first fastening member is a fastener tape, and the first fastening element is self-adhesive coated on the outer surface of the base sheet of said first fastening member; and
said second fastening member is a target tape strip made of a plastic material to which said self-adhesive of said tape fastener is releasably adherable.

11. The wearing article according to claim 1, further comprising
a liquid-pervious topsheet adapted to face a wearer's body, in use;
a liquid-impervious backsheet adapted to face away from said wearer's body, in use; and
a liquid-absorbent panel interposed between said topsheet and backsheet.

12. The article according to claim 1, wherein at least one of said first and second fastening members obliquely extends toward said crotch region and gets nearer to a longitudinal center line bisecting a width, measured in said transverse direction, of the one of said front and rear waist regions.

13. The article according to claim 1, wherein said second fastening member is engageable with said first fastening member only if the one of said front and rear waist regions is folded to form a pleat in a vicinity of at least one of said first and second fastening members.

14. The article according to claim 1, wherein transversely opposite lateral zones of said front and rear waist regions are permanently bonded to each other to define a waist hole and a pair of leg holes.

15. A pull-on disposable wearing article, comprising:
a front waist region;
a rear waist region;
a crotch region between said front and rear waist regions;
a waist-hole;
a pair of leg-holes; and
one of said front and rear waist regions having:
fastening members, and
at least one landing member juxtaposed with said fastening members in a waist-circumferential direction of the one of said front and rear waist regions to releasably engage with said fastening members;
wherein
said fastening members are secured to transversely opposite lateral zones of the one of said front and rear waist regions;
said at least one landing member is secured to a middle zone of the one of said front and rear waist regions, said middle zone being located between said lateral zones; and
said fastening members obliquely extend, from a vicinity of said waist-hole toward said leg-holes so that said fastening members get nearer to a longitudinal center line bisecting a width, measured in said waist-circumferential direction, of the one of said front and rear waist regions.

16. A pull-on disposable wearing article, comprising:
a front waist region;
a rear waist region;
a crotch region extending in a longitudinal direction between said front and rear waist regions;
a fastening member; and
a landing member releasably engageable with said fastening member;
wherein
transversely opposite lateral zones of said front and rear waist regions are permanently bonded to each other at bonding sites to define a waist hole and a pair of leg holes;
a width, measured in a transverse direction between the bonding sites, of one of said front and rear waist regions is larger than that of the other one of said front and rear waist regions;
said one of said front and rear waist regions is free of elastic material along a periphery of said waist hole;
said one of said front and rear waist regions has an outer surface facing away from the other one of said front and rear waist regions;
both said fastening and landing members are disposed on said outer surface of said one of said front and rear waist regions, with the landing member being juxtaposed with said fastening members in said transverse direction; and
at least one of said fastening and landing members obliquely extends toward said crotch region and gets nearer to a longitudinal center line bisecting the width of the one of said front and rear waist regions.

17. A pull-on disposable wearing article, comprising:
a front waist region;
a rear waist region;
a crotch region extending in a longitudinal direction between said front and rear waist regions;
a fastening member; and
a landing member releasably engageable with said fastening member;
wherein
transversely opposite lateral zones of said front and rear waist regions are permanently bonded to each other at bonding sites to define a waist hole and a pair of leg holes;
a width, measured in a transverse direction between the bonding sites, of one of said front and rear waist regions is larger than that of the other one of said front and rear waist regions;
said one of said front and rear waist regions is free of elastic material along a periphery of said waist hole;
said one of said front and rear waist regions has an outer surface facing away from the other one of said front and rear waist regions;
both said fastening and landing members are disposed on said outer surface of said one of said front and rear waist regions, with the landing member being juxtaposed with said fastening members in said transverse direction; and said landing and fastening members are engageable one with another only if the one of said front and rear waist regions is folded to form a pleat in a vicinity of at least one of said landing and fastening members.

18. A pull-on disposable wearing article, comprising:

a front waist region;

a rear waist region;

a crotch region extending in a longitudinal direction between said front and rear waist regions;

a fastening member; and a landing member releasably engageable with said fastening member;

wherein transversely opposite lateral zones of said front and rear waist regions are permanently bonded to each other at bonding sites to define a waist hole and a pair of leg holes;

a width, measured in a transverse direction between the bonding sites, of one of said front and rear waist regions is larger than that of the other one of said front and rear waist regions;

said one of said front and rear waist regions is free of elastic material along a periphery of said waist hole;

said one of said front and rear waist regions has an outer surface facing away from the other one of said front and rear waist regions;

both said fastening and landing members are disposed on said outer surface of said one of said front and rear waist regions, with the landing member being juxtaposed with said fastening members in said transverse direction; and said article comprises:

two said fastening members which are secured to the transversely opposite lateral zones of the one of said front and rear waist regions; and two said landing members which are spaced from each other in said transverse direction and secured to a middle zone of the one of said front and rear waist regions, said middle zone being located between said lateral zones.

* * * * *